(12) United States Patent
Bassler et al.

(10) Patent No.: US 7,544,818 B2
(45) Date of Patent: Jun. 9, 2009

(54) CONTINUOUS RECIRCULATION OF THE OLEFIN WHICH HAS NOT BEEN REACTED IN THE OXIDATION OF OLEFINS BY HYDROPEROXIDES, BY MEANS OF SOLVENT SCRUBBING

(75) Inventors: Peter Bassler, Viernheim (DE);
Hans-Georg Goebbel, Kallstadt (DE);
Joaquim Henrique Teles, Otterstadt (DE); Peter Rudolf, Ladenburg (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 416 days.

(21) Appl. No.: 10/531,868

(22) PCT Filed: Oct. 23, 2003

(86) PCT No.: PCT/EP03/11735

§ 371 (c)(1),
(2), (4) Date: Apr. 19, 2005

(87) PCT Pub. No.: WO2004/037390

PCT Pub. Date: May 6, 2004

(65) Prior Publication Data

US 2006/0167287 A1 Jul. 27, 2006

(30) Foreign Application Priority Data

Oct. 23, 2002 (DE) .................................. 102 49 379

(51) Int. Cl.
*C07D 301/06* (2006.01)
*C07D 301/12* (2006.01)
*C07D 301/19* (2006.01)

(52) U.S. Cl. .................. 549/524; 549/529; 549/531

(58) Field of Classification Search .................. 549/525, 549/526, 524, 529, 531
See application file for complete search history.

(56) References Cited

U.S. PATENT DOCUMENTS 5,599,955 A 2/1997 Vora et al.

FOREIGN PATENT DOCUMENTS

| DE | 1 212 507 | 3/1966 |
| EP | 0 583 828 | 2/1994 |
| EP | 0 719 768 | 7/1996 |
| WO | 00/07965 | 2/2000 |
| WO | 01/96271 | 12/2001 |
| WO | 02/102496 | 12/2002 |

OTHER PUBLICATIONS

Aldrich, 1998-1999, p. 1560, (2 pages).*

* cited by examiner

*Primary Examiner*—Taylor Victor Oh
(74) *Attorney, Agent, or Firm*—Oblon, Spivak, McClelland, Maier & Neustadt, P.C.

(57) ABSTRACT

Process for the continuous recirculation of the olefin which has not been reacted in the oxidation of olefins by means of hydroperoxide to give oxiranes and is present in the offgas stream formed during the oxidation, which comprises the steps (i) to (iii)
(i) separating the olefin from the offgas stream by absorption in a hydrocarbon,
(ii) desorbing the olefin from the hydrocarbon,
(iii) recirculating the olefin obtained in step (ii) to the oxidation process.

11 Claims, 2 Drawing Sheets

Figure 1:
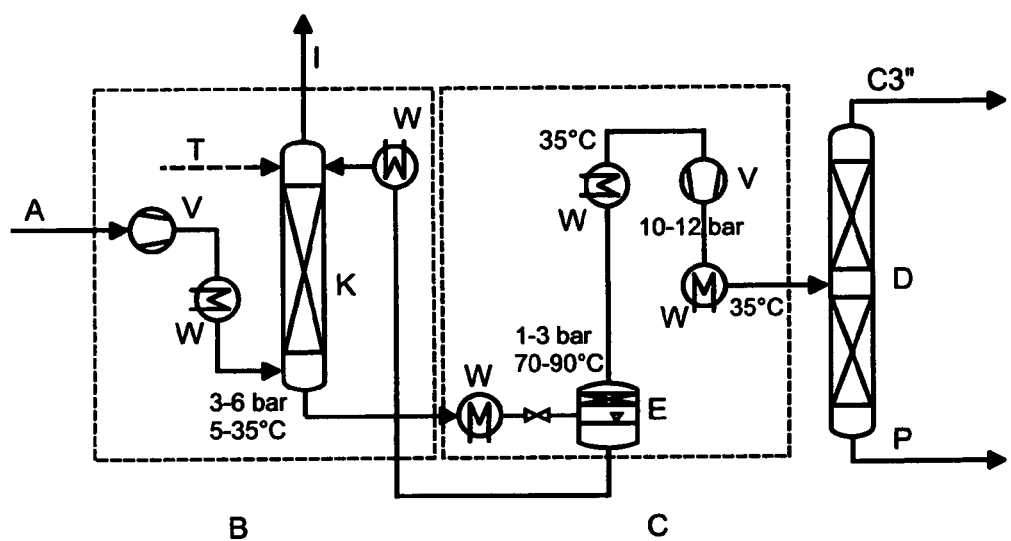

CONTINUOUS RECIRCULATION OF THE OLEFIN WHICH HAS NOT BEEN REACTED IN THE OXIDATION OF OLEFINS BY HYDROPEROXIDES, BY MEANS OF SOLVENT SCRUBBING

The invention relates to a process for the continuous recirculation of the olefin which has not been reacted in the oxidation of olefins by means of hydroperoxides to give oxiranes, in which the olefin is firstly absorbed from the offgas stream formed in the oxidation in a solvent comprising hydrocarbons, preferably tetradecane, subsequently desorbed therefrom, possibly freed of aliphatics, and recirculated to the oxidation process. The process can be employed particularly advantageously for the recirculation of the propene used in the preparation of propene oxide. The invention also relates to an apparatus by means of which the process can be carried out.

It is known that in the oxidation of olefins by means of hydroperoxides to give oxiranes, the selectivity of oxirane formation decreases significantly and the level of undesirable secondary reactions increases as the olefin conversion rises. To be able to achieve a high selectivity of over 95% despite this, these reactions are, especially on an industrial scale, therefore preferably carried out only to an olefin conversion of about 85-95%.

Isolating the unreacted olefin from the reaction process and then recirculating it to the oxidation process is also known.

Thus, a process in which a gas mixture comprising the olefin and oxygen originating from the decomposition reaction of the hydrogen peroxide used as hydroperoxide in the oxidation is separated off and the olefin is absorbed from the gas mixture in a liquid absorption medium has been proposed. In this process, a sufficient amount of an inert gas is added to the oxygen to prevent formation of flammable gas compositions (EP-B 0 719 768 B1). In a preferred embodiment, this process is used for recovering propene from the reaction of propene with hydrogen peroxide to give propene oxide. The inert gas used is preferably methane and the liquid absorption medium used is a mixture comprising isopropanol and water. Hydrocarbons such as heptane and octane and also methanol and acetone can also be used, but less advantageously, in this process.

However, a disadvantage of the abovementioned process is that a further gas, in particular methane, in addition to the offgas stream has to be fed into the column used for the absorption. This measure is intended to prevent the formation of explosive mixtures in the gas mixture as a result of the oxygen content.

The low solubility of the olefin in water-containing isopropanol is also a disadvantage in this process. For example, based on the description, it is necessary to use solvent mixtures which have a water content of from 30.6 mol % to 57.2 mol %. This high water content reduces the solubility of the olefin in the isopropanol. For this reason, relatively large amounts of solvent have to be used in order to be able to recover the olefin from the offgas stream by absorption.

It is an object of the present invention to provide an improved process for recovering the olefin used in the oxidation of olefins to oxiranes, which makes do without the additional introduction of an inert gas into the absorber column and by means of which more effective recovery of the olefin from the offgas stream can be achieved than is possible in the process of the prior art.

We have found that this object is achieved by firstly separating the olefin which has not been reacted in the oxidation of an olefin by means of hydroperoxide to give the oxirane and is present in the offgas stream from the offgas stream by absorption in a hydrocarbon, preferably tetradecane, in an absorption plant, liberating it therefrom by desorption and recirculating it to the oxidation process.

The present invention accordingly provides a process for the continuous recirculation of the olefin which has not been reacted in the oxidation of olefins by means of hydroperoxide to give oxiranes and is present in the offgas stream formed during the oxidation, which comprises the steps (i) to (iii)
(i) separating the olefin from the offgas stream by absorption in a hydrocarbon,
(ii) desorbing the olefin from the hydrocarbon,
(iii) recirculating the olefin obtained in step (ii) to the oxidation process.

The hydrocarbon obtained in step (ii) after desorption of the olefin is preferably recirculated to step (i).

The oxidation of olefins by means of hydroperoxides to give oxiranes is known and can be carried out by known methods. Such methods and an industrial process are described, for example, in WO 00/07965.

To separate off the oxiranes formed in the oxidation from the reaction mixtures, it is possible to use, for example, distillation columns. Here, offgas streams are obtained at the top of the columns. These offgas streams always comprise unreacted olefin and a small amount of oxygen which originates from the decomposition reaction of the hydroperoxide used. To obtain better regulation of the distillation, it is customary to use inert gases, preferably nitrogen. Since these are likewise taken off at the top of the columns, the offgas streams further comprise these gases. It is therefore no longer necessary to feed an additional gas into the absorption plant to avoid explosive mixtures in the process of the present invention.

Furthermore, the hydrocarbons used as absorption medium have an excellent solvent capacity for olefins, so that the process can be carried out using comparatively small amounts of absorption medium. The novel process is therefore extremely advantageous for industrial use.

The term hydrocarbons encompasses aliphatic, cyclic, alicyclic, saturated, unsaturated and aromatic hydrocarbons which may also be substituted by aliphatic radicals. The hydrocarbons can also be used in the form of mixtures in the process of the present invention. The hydrocarbons preferably have more than 10 carbon atoms in the molecule.

Preference is given to using tetradecane as hydrocarbon.

For the present purposes, the term tetradecane encompasses a mixture of long-chain hydrocarbons of the formula $C_nH_{2n+2}$, where n is an integer from 10 to 20, preferably from 13 to 15. The component tetradecane of the formula $C_{14}H_{30}$ should be present in this mixture in a proportion of preferably at least 10% by weight, more preferably at least 30% by weight, in particular at least 50% by weight, wherein the sum of all components present in the mixture is 100% by weight. Accordingly, it is not necessary for the tetradecane used in the process of the present invention to have a particularly high purity. The mixture described can, for example, be obtained in the refining of crude oil, with the mixture corresponding to the desired fraction being taken off. Further components which can as a result be present in addition to the tetradecane are further saturated hydrocarbons which may also be branched or unbranched, long-chain, cyclic or alicyclic. Unsaturated hydrocarbons or aromatic hydrocarbons may also be present in such a mixture.

The hydrocarbon or hydrocarbon mixture, in particular tetradecane or a hydrocarbon mixture comprising tetradecane, used for absorption preferably has a boiling point of from 200 to 300° C., more preferably from 220 to 270° C.

Such a hydrocarbon or hydrocarbon mixture displays an extremely advantageous solvent capacity for the olefins used in olefin oxidation by means of hydroperoxides, in particular for propene. Tetradecene or hydrocarbon mixtures comprising tetradecene display this advantageous solvent capacity to a particular extent.

To carry out the process of the present invention, the offgas stream originating from a process for the oxidation of an olefin to an oxirane (epoxidation), which may also be a combination of a plurality of offgas streams, is then advantageously compressed to a pressure of from 2 to 10 bar, preferably from 3 to 6 bar, by means of a compressor, subsequently cooled to preferably from 5 to 35° C. by means of cold water and fed to an absorption plant for the purpose of separating off the olefin.

Such absorption plants preferably comprise the absorption apparatus and a downstream desorption apparatus. End products from such a plant are always the gas separated off by selective absorption and the tailgas mixture. In addition, the regenerated absorption medium is obtained, and this is recirculated to the absorption apparatus.

In the absorption plant, it is possible to use packed columns, tray columns and bubble columns and in special cases Venturi scrubbers, preferably operating in countercurrent. In the overall plant, the absorption and desorption apparatuses are connected to form a continuously operating unit.

The offgas stream from the oxidation process is firstly fed into the absorption apparatus, preferably in the lower part, while the hydrocarbon is fed into the upper part. This results in pronounced countercurrent flow of the streams. Further introduction of additional inert gas, as is necessary in the process disclosed in the prior art, is not necessary since the offgas stream already contains components from the process, preferably nitrogen, which prevent the formation of an explosive atmosphere.

The pressure of from 2 to 10 bar, preferably from 3 to 6 bar, prevailing in the absorption apparatus increases the solubility of the soluble constituents of the offgas stream, in particular the unreacted olefin, in the hydrocarbon, which is preferably tetradecane. The pure, insoluble gas constituent then leaves the absorption apparatus at the top of the column. This preferably comprises nitrogen, oxygen and small amounts of olefin, for example propene if this is used in the oxidation process.

Due to the proportion of inert gases in the offgas stream from the oxidation, the separation occurs outside the range in which explosive mixtures with oxygen can be formed. Additional introduction of further gases to form nonexplosive mixtures therefore becomes superfluous. This insoluble gas can, for example, be passed to incineration.

The olefin-laden hydrocarbon obtained at the bottom of the column is passed to the desorption stage. There are two possible ways of carrying out the desorption; these are virtually equivalent and the choice between them depends on the availability of a refrigeration plant.

If a refrigeration plant using brine (about −35° C.) is available, the desorption is preferably carried out in a distillation column at a pressure of from 1 to 3 bar. In this case, the olefin is freed of hydrocarbons in the column and separated off in liquid form via the top of the column, brought to a higher pressure level as liquid by means of a conventional pump and fed either directly to the reaction stage or to a further purification stage. The hydrocarbon freed of olefin is obtained at the bottom and this is cooled and subsequently recirculated to the absorption column.

If no refrigeration plant is available, it is useful to carry out the desorption as a single-stage expansion vaporization, also known as flash evaporation, at a pressure of from 1 to 3 bar and a temperature of from 50 to 100° C., preferably from 70 to 90° C. In this case, the olefin is separated off in gaseous form and cooled in a downstream heat exchanger, for example to about 35° C. or to room temperature. The cooled gas stream is compressed to a pressure of about 11 to 12 bar by means of a compressor, so that it can be liquefied using normal river water as coolant.

Suitable compressors are, for example, piston compressors. The hydrocarbon remaining after the vaporization step in this case still contains small concentrations of the olefin. If propene is used as olefin, the proportion is about 1% by weight. The hydrocarbon is cooled in a heat exchanger and recirculated to the absorption stage. The liquefied gas stream can then be fed either directly to the reaction stage or to a further purification stage.

In a preferred embodiment of the process of the invention, the olefin is accordingly absorbed at a pressure of from 3 to 6 bar and a temperature of from 5 to 35° C. and separated off in liquid form at a pressure of from 1 to 3 bar at the top of a distillation column or in gaseous form at a pressure of from 1 to 3 bar and a temperature of from 70 to 90° C. by means of flash evaporation.

In a further embodiment it is possible to operate the absorption plant in the form of an extraction plant. This is of particular interest when the olefin to be separated off cannot be desorbed in gaseous form from the hydrocarbon on depressurization of the apparatus, but instead forms a liquid phase. Suitable plants comprise, for example, a countercurrent extraction apparatus provided with downstream rectification columns for working up the hydrocarbon and the liquid olefin.

The olefin, which is preferably obtained in a purity of at least 95%, can then be returned without further purification steps to the oxidation by the hydroperoxide.

A particularly advantageous aspect of the process of the present invention is that the olefin can be recirculated to the oxidation process in the amount in which it is separated off from the offgas stream from the oxidation. This makes possible an economically extremely advantageous process which can be operated continuously.

In a preferred embodiment of the process of the present invention, the offgas stream further comprises other components, for example saturated hydrocarbons, in addition to the olefins. The saturated hydrocarbons may already have been present in the feed olefin.

Propene is preferably used as olefin in the oxidation stage. This preferably contains propane as saturated hydrocarbon. Preference is given to using fractions which comprise propene and propane in a volume ratio of from about 97:3 to 95:5. Such mixtures are also referred to as "chemical grade" propene. Preference is given to using propene of this purity in the preparation of propene oxide.

In a particularly preferred embodiment of the process of the present invention, the offgas stream from the conversion of propene into propene oxide therefore comprises propene as olefin and propane as saturated hydrocarbon.

As indicated above, the offgas stream then comprises not only the propene and propane but also inert gases, in particular nitrogen, and a small amount of oxygen.

In the process of the present invention, the offgas which has been freed of propene and propane is separated off at the top of the absorption apparatus and the hydrocarbon, preferably tetradecane, laden with propene and propane is separated off at the bottom of the column.

In the subsequent desorption step, the mixture of propene and propane is separated either in liquid or gaseous form from the hydrocarbon at a pressure of from about 1 to 3 bar using one of the above-described embodiments. The hydrocarbon is cooled and recirculated to the absorption stage.

The resulting stream comprising the low-boiling components propene and propane can subsequently be separated into the components propene and propane in a $C_3$ splitter as described, for example, in Ullmann's Encyclopedia of Industrial Chemistry, 5$^{th}$ Edition, Volume A22, page 214. The separation can be carried out in a column at a pressure of from about 15 to 25 bar. The separation can also be carried out using thermally coupled columns, and these are, for example, operated at a pressure of about 15 or 25 bar. The propene is taken off at the top of the $C_3$ splitter configured as a column, and the propane is taken off at the bottom.

Accordingly, another embodiment of the process of the present invention provides for the propene/propane mixture obtained after separation from the hydrocarbon to be separated into propene and propane in a $C_3$ splitter.

The propene which has been separated off can then be returned to the oxidation by the hydroperoxide. The propane can be used as energy source for steam generation.

Examples of olefins which can be separated off by means of the process of the present invention from offgas streams which are formed in the oxidation of these olefins by means of hydroperoxide to give the corresponding oxiranes are the following compounds:

ethene, propene, 1-butene, 2-butene, isobutene, butadiene, pentenes, piperylene, hexenes, hexadienes, heptenes, octenes, diisobutene, trimethylpentene, nonenes, dodecene, tridecene, tetradecenes to eicosenes, tripropene and tetrapropene, polybutadienes, polyisobutenes, isoprenes, terpenes, geraniol, linalool, linalyl acetate, methylenecyclopropane, cyclopentene, cyclohexene, norbornene, cyclo-heptene, vinylcyclohexane, vinyloxirane, vinylcyclohexene, styrene, cyclooctene, cyclooctadiene, vinylnorbornene, indene, tetrahydroindene, methylstyrene, dicyclopentadiene, divinylbezene, cyclododecene, cyclododecatriene, stilbene, diphenylbutadiene, vitamin A, beta-carotene, vinylidene fluoride, allyl halides, crotyl chloride, methallyl chloride, dichlorobutene, allyl alcohol, methallyl alcohol, butenols, butenediols, cyclopentenediols, pentenols, octadienols, tridecenols, unsaturated steroids, ethoxyethene, isoeugenol, anethole, unsaturated carboxylic acids such as acrylic acid, methacrylic acid, crotonic acid, maleic acid, vinylacetic acid, unsaturated fatty acids such as oleic acid, linoleic acid, palmitic acid, naturally occurring fats and oils.

Hydroperoxides which can be used for the oxidation are all the hydroperoxides which are known from the prior art and are suitable for reaction with the olefin. Examples of such hydroperoxides are tert-butyl hydroperoxide and ethylbenzene hydroperoxide. Hydrogen peroxide can also be used as hydroperoxide, for example as an aqueous solution.

The offgas streams can also originate from oxidation processes in which the reaction of the olefin with the hydroperoxide is catalyzed, for example by means of heterogeneous catalysts.

In a particularly preferred embodiment of the process of the present invention, propene is separated off from an offgas stream obtained in the oxidation of propene by means of hydrogen peroxide to give propene oxide. Tetradecane is preferably used as hydrocarbon for this separation.

The invention likewise provides an apparatus for carrying out the process of the present invention, which comprises at least one reactor for preparing the oxirane, at least one absorption and desorption unit for separating off the olefin and a $C_3$ splitter.

Figure 2:
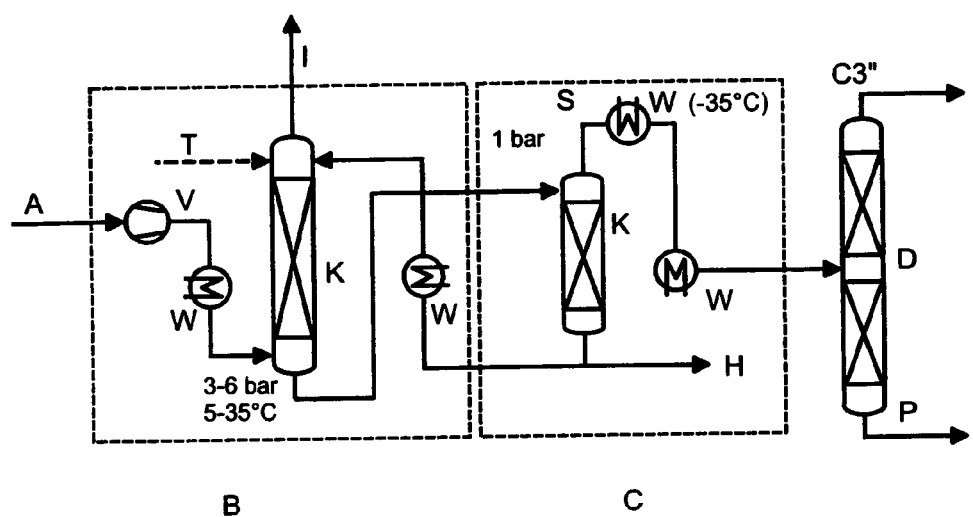

The flow diagrams shown in FIGS. 1 and 2 indicate how propene can be recovered according to the present invention by means of a tetradecane scrub from an offgas stream formed in the epoxidation (oxidation) of propene to propene oxide. FIG. 1 shows the recovery without using a refrigeration plant and FIG. 2 shows the recovery when a refrigeration plant is available.

LIST OF REFERENCE NUMERALS FOR THE FIGURES

FIG. 1:
A Offgas from oxidation
B Absorption unit
  V Compressor
  W Heat exchanger
  K Column
  T Tetradecane
  I Inert gases ($N_2$), $O_2$
C Desorption unit
  V Compressor
  E Vessel for flash evaporation
  W Heat exchanger
D C3 splitter
  P Propane (and high boilers)
  C3" "Chemical grade" propene FIG. 2:
A Offgas from oxidation
B Absorption unit
  V Compressor
  W Heat exchanger
  T Tetradecane
  K Column
  I Inert gases ($N_2$), $O_2$
C Desorption unit
  S Cooling brine (−35° C.)
  W Heat exchanger
  H High boilers
  K Column
D C3 splitter
  P propane
  C3" "Chemical grade" propene

We claim:

1. A process for the continuous recirculation of the propene which has not been reacted in the oxidation of propene by means of hydroperoxide to give propene oxide, said propene is a mixture comprising propene and propane in a volume ratio of from about 97:3 to 95:5 and is present in the offgas stream formed during the oxidation, which comprises the steps of (i) to (iii):

(i) separating the propene and propane from the offgas stream by absorption in a hydrocarbon mixture, (ii) desorbing the propene and propane from the hydrocarbon mixture, wherein the mixture of propene and propane is separated off either in liquid form in a distillation column at a pressure of from 1 to 3 bar or in gaseous form at a pressure of from 1 to 3 bar and a temperature of from 50 to 100° C. in a flash evaporation, (iii) recirculating the propene obtained in step (ii) to the oxidation process, wherein the propene/propane mixture obtained after separation from the hydrocarbon mixture is separated into propene and propane in a $C_3$ splitter before recirculating the propene to the oxidation process, and the hydrocarbon mixture is a mixture of long chain hydrocarbons of the formula:

$$C_nH_{2n+2}$$

wherein n is an integer of from 13 to 15, and the mixture comprises a tetradecane of the formula $C_{14}H_{30}$ in an amount of at least 10% by weight.

2. The process as claimed in claim 1, wherein the hydrocarbon mixture obtained after desorption of the olefin in step (ii) is recirculated to step (i).

3. The process as claimed in claim 1, wherein the hydrocarbon mixture is tetradecane.

4. The process as claimed in claim 2, wherein the hydrocarbon mixture is tetradecane.

5. The process as claimed in claim 1, wherein the propene is absorbed at a pressure of from 3 to 6 bar and a temperature of from 5 to 35° C.

6. The process as claimed in claim 2, wherein the propene is absorbed at a pressure of from 3 to 6 bar and a temperature of from 5 to 35° C.

7. The process as claimed in claim 3, wherein the propene is absorbed at a pressure of from 3 to 6 bar and a temperature of from 5 to 35° C.

8. The process as claimed in claim 1, wherein the offgas stream comprises inert gases and a small amount of oxygen.

9. The process as claimed in claim 2, wherein the offgas stream comprises inert gases and a small amount of oxygen.

10. The process as claimed in claim 8, wherein the offgas stream comprises nitrogen.

11. The process as claimed in claim 9, wherein the offgas stream comprises nitrogen.

* * * * *